United States Patent [19]

Poortmann et al.

[11] Patent Number: 5,719,340

[45] Date of Patent: Feb. 17, 1998

[54] PROCESS FOR DETERMINING THE PHASE PORTION OF A FLUID MEDIUM IN OPEN AND CLOSED PIPES

[75] Inventors: Boudewijn Jozef Poortmann, Dordtrecht; Heerke Nijboer, Barendrecht; Aart Jan van Bekkum, Hoornaar, all of Netherlands

[73] Assignee: Krohne AG, Basel, Switzerland

[21] Appl. No.: 697,288

[22] Filed: Aug. 26, 1996

[30] Foreign Application Priority Data

Aug. 24, 1995 [DE] Germany ............. 195 31 124.8

[51] Int. Cl.$^6$ ............................................. G01F 1/56
[52] U.S. Cl. ............................. 73/861.08; 73/861.04
[58] Field of Search .................... 73/718, 724; 324/686, 324/688, 687, 690

[56] References Cited

U.S. PATENT DOCUMENTS

| | | | |
|---|---|---|---|
| 3,635,082 | 1/1972 | Prellwitz et al. | 73/861.04 |
| 4,752,727 | 6/1988 | Schneider | 324/688 X |
| 5,017,879 | 5/1991 | Lucas et al. | 324/686 X |
| 5,130,661 | 7/1992 | Beck et al. | 324/687 X |
| 5,287,752 | 2/1994 | Den Boer | 73/861.04 |
| 5,291,791 | 3/1994 | Lucas et al. | 73/861.08 |
| 5,421,210 | 6/1995 | Kobayashi et al. | 73/861.08 X |

FOREIGN PATENT DOCUMENTS

| | | | |
|---|---|---|---|
| 308004-A | 3/1989 | European Pat. Off. | 324/688 |
| 0 514 964 A2 | 11/1992 | European Pat. Off. | |
| 0 547 751 A2 | 6/1993 | European Pat. Off. | |
| 63-145919 | 6/1988 | Japan | 73/861.08 |

*Primary Examiner*—George M. Dombroske
*Assistant Examiner*—Paul D. Amrozowicz
*Attorney, Agent, or Firm*—Cesari and McKenna, LLP

[57] ABSTRACT

A process for determining the phase portion of a medium in open and closed pipes, especially for use in connection with a process for determining the volume flow, with the help of at least three condenser plates extending basically over the entire height of the pipe and with the help of a control and evaluation circuit, in which at least one of the condenser plates has an alternating voltage applied to it by the control and evaluation circuit and the current flowing between the condenser plate with the voltage appled to it and at least one other condenser plate is recorded by the control and evaluation circuit. The process is designed so that the current between at least two condenser plates is recorded by the control and evaluation circuit from two different groups of condenser plates separated by the vertical line of the pipe. The current between individual condenser plates in the first group of condenser plates and at least one condenser plate in the second group of condenser plates is recorded by the control and evaluation circuit in sequence; the current of the highest plate reached by the surface level of the medium in the first group of condenser plates is standardized by the control and evaluation circuit using the currents of the lower-lying condenser plates in the first group of condenser plates; and the standardized current from the highest condenser plate reached by the surface level of the medium in the first group of condenser plates is evaluated as a measurement for the position of the surface level of the medium relative to the highest condenser plate reached by the surface level of the medium in the first group of condenser plates.

17 Claims, 5 Drawing Sheets

PROCESS FOR DETERMINING THE PHASE PORTION OF A FLUID MEDIUM IN OPEN AND CLOSED PIPES

FIELD OF THE INVENTION

The invention concerns a process for determining the phase portion of a fluid medium in open and closed pipes, especially for use in connection with a process for determining the volume flow using at least three condenser plates extending in toto basically over the entire height of the pipe, and using a control and evaluation circuit, in which at least one of the condenser plates has an alternating voltage applied to it by the control and evaluation circuit and the current flowing between the condenser plate with the voltage applied to it and at least one other condenser plate is recorded by the control and evaluation circuit.

BACKGROUND OF THE INVENTION

The above-mentioned process is known from EP A 0 514 964. In the known process, preferably ten condenser plates are arranged around one pipe, and they are controlled by a control and evaluation circuit so that a circulating electrical field is produced in the pipe. In the known process, after an integral number of circulations of the electrical field, the average capacity of the pipe, including the medium in the pipe, is determined. Once the electrical properties of the medium are known, the portion of liquid and gaseous phase of the medium can be calculated from that capacity. The problem with this known process is that, as explained, the portion of liquid and gaseous phase of the medium can be determined only by knowing the electrical properties, and especially the dielectric constant $\epsilon$ and the electrical conductivity $\sigma$. This is a problem because the electrical properties of the medium are constantly changing if the medium is not homogeneous, and the electrical properties of the medium are also dependent on its temperature, which in most cases is not constant.

The publication EP A 0 547 751 also describes a method for determining the phase portion of a medium in open and closed pipes. In this known process, as in the magnetically inductive principle for measuring volume flow, the phase portion is determined using a magnetic field perpendicular to the pipe and electrodes, arranged horizontally on the sides of the pipe. In this known process, as in the known process on which the invention is based, the problem is that the electrical properties of the medium must be known to determine the phase portion. Another problem with this known process is that the phase portion cannot be determined at all if the medium is standing in the pipe, not flowing through it.

SUMMARY OF THE INVENTION

The invention is therefore based on the task of developing the known process for determining the phase portion of a medium in open and closed pipes and designing it in such a way that the phase portion of the medium can be determined without knowing the electrical properties of the medium, even for a medium standing still in the pipe.

The process of this invention for determining the phase portion of a medium in open and closed pipes, which solves the problem introduced and described here, is characterized by the fact that: the current is recorded by the control and evaluation circuit between at least two condenser plates out of two different groups of condenser plates separated by the vertical axis of the pipe; the current between the individual condenser plates in the first group of condenser plates and at least one condenser plate in the second group of condenser plates is recorded by the control and evaluation circuit in sequence; the current of the highest condenser plate reached by the surface level of the medium in the first group of condenser plates is standardized by the control and evaluation circuit using the current of the lower-lying condenser plates in the first group of condenser plates; and the standardized current of the highest condenser plate reached by the surface level of the medium in the first group of condenser plates is evaluated by the control and evaluation circuit as a measurement for the position of the surface level of the medium relative to the highest condenser plate reached by the surface level of the medium in the first group of condenser plates.

The design of the process according to the invention guarantees that the phase portion of the medium in the pipe, based on standardization without the influence of the electrical properties, can be determined regardless of the electrical properties, particularly, the dielectric constant $\epsilon$ and the electrical conductivity $\sigma$ of the medium. Since the process of the invention is based on determining the capacity between two condenser plates with the medium between them, it provides measured values for the phase portion of the medium in the pipe, regardless of the flow speed of the medium.

One first advantageous embodiment of the invention provides that the current in the highest condenser plate reached by the surface level of the medium in the first group of condenser plates is standardized, using the sum of the currents of the lower-lying condenser plates in the first group of condenser plates. Since the sum of the currents of the lower-lying condenser plates in the first group of condenser plates has a higher absolute value than, for example, the current in the condenser plate lying under the highest condenser plate reached by the surface level of the medium in the first group of condenser plates, the measurement precision caused by standardization in the measurement result for the phase portion is greater.

Now, if the process according to the invention is designed so that one after another, the currents from all sequences of condenser plates in the first group of condenser plates starting with the lowest condenser plate in the first group of condenser plates are recorded by the control and evaluation circuit, this further increases the measurement accuracy of the process of the invention. In this case, the standardization described in the previous paragraph can be done using a single measured value for the current of one sequence of condenser plates in the first group of condenser plates starting with the lowest condenser plates in the first group of condenser plates. Unlike adding the individual measured values recorded, this has an advantage in measurement accuracy for the sum of the currents of the lower-lying condenser plates in the first group of condensers.

To guarantee a quantitative evaluation of the standardized currents of the highest condenser plate reached by the surface level of the medium in the first group of condenser plates, the process of the invention is further designed so that in a calibration process for each condenser plate in the first group of condenser plates, the standardized current for a surface level of the medium on the upper edge of the condenser plate is recorded.

In the event that a condenser plate in the first group of condenser plates directly reaches the lower edge of the surface level of the medium, one can either neglect the capacity influenced exclusively by the gaseous phase of the medium and assume that the standardized current of the condenser plate is zero in this case, or one can further design the process of the invention for increased measurement accuracy, so that the standardized current is recorded in the first group calibration process for each condenser plate in the first group of condenser plates at a surface level of the medium on the lower edge of the condenser plate. In this case, the capacity basically determined by the gaseous phase of the medium between the respective condenser plate in the first group of condenser plates and the condenser plates in the second group of condenser plates is considered and thus the measurement accuracy is increased.

Evaluating the standardized current in the highest condenser plate reached by the surface level of the medium in the first group of condenser plates is simplified by the fact that the standardized current for each condenser plate in the first group of condenser plates between a surface level of the medium on the lower edge and a surface level of the medium on the upper edge of the respective condenser plate is assigned by the control and evaluation circuit linearly to the height of the medium relative to the respective condenser plate.

If the second group of condenser plates also consists of several condenser plates, the process of the invention is also guaranteed to be simplified, because the current on condenser plates switched together in the second group of condenser plates is recorded by the control and evaluation circuit.

Alternatively to the last measure described, the process according to the invention is advantageously designed when the current for condenser plates in the second group of condenser plates switched corresponding to the condenser plates in the first group of condenser plates is recorded by the control and evaluation circuit. This guarantees that basically only the medium found between two opposite condenser plates in the first and second group of condenser plates influences the current.

One especially advantageous design of the process of the invention provides that when the medium is at a very low surface level, the volume flow is determined directly from the height of the surface level of the medium. Very low surface levels of the medium means those surface levels in which the flow speed of the medium is basically determined by the surface roughness of the wall of the pipe and the inclination of the transducer. In such cases of very low surface levels, the known process for volume flow measurements regularly fails. Here the design of the process in the invention described above provides help.

Lastly, the process of the invention has another design in which the conductivity and/or the dielectric constant of the medium is determined by the control and evaluation circuit. The possibility of determining the conductivity and/or the dielectric constants of the medium expands the measurement of the phase portion described above because if the composition of the medium is known, for example the density of the medium in the liquid phase can be deduced.

Besides the design of the process according to the invention, the advantageous design of a device for implementing the process of the invention with at least three condenser plates extending in tote basically over the entire height of the pipe and a control and evaluation circuit plays an important role in carrying out the process in the invention. The design of this device, basically known from EP A 0 514 964, is very advantageous in carrying out the process in the invention because: at least two, but preferably four, condenser plates form a first group of condenser plates; at least one condenser plate forms a second group of condenser plates; and the first group of condenser plates and the second group of condenser plates are separated from one another by the vertical axis of the pipe. This design of the known device makes it possible to carry out the process of the invention.

Since it takes at least two condenser plates in the first group of condenser plates which must be at least reached by the surface level of the medium to carry out the invention process, the device is designed especially advantageously in that the lowest condenser plate in the first group of condenser plates covers a lower height than the other condenser plates in the first group of condenser plates. This guarantees that the lowest condenser plate in the first group of condenser plates is under the surface level of the medium when the medium is already at a low level. This ensures standardization of the currents of the condenser plates above it in the first group of condenser plates.

So that simplifications of the process of the invention described does not lead to an increase in measurement inaccuracy by having the standardized current for each condenser plate in the first group of condensers assigned linearly between a surface level of the medium on the lower edge and a surface level of the medium on the upper edge of the respective condenser plate to the height of the medium relative to the respective condenser plate, it is advantageous to design the device for carrying out the invention process so that the width of the condenser plates, depending on the height of the pipe, is always proportional to the width of the pipe at the respective height. This measure guarantees that the current assigned to the condenser plate is proportional to the height of the surface level of the medium.

To protect the condenser plates from potential chemically corrosive media, the device for carrying out the invention process is advantageously designed so that the condenser plates are at least basically embedded in an insulating lining of the pipe. Such a lining is generally inside the pipe and made of PTFE, PFA, polyurethane, rubber or the like.

One especially advantageous embodiment of the device for carrying out the process of the invention, especially when used in connection with the magnetically inductive method of measuring volume flow is that one condenser plates in each of the first and second group of condenser plates are in contact with the medium and are used as electrodes for a magnetically inductive volume flow meter. This guarantees that no other electrodes must be used as components of a magnetically inductive volume flow meter in the pipe.

The fact that at least two, and preferably four condenser plates, form the second group of condenser plates guarantees that the process in the invention can also be carried out with interchanged roles in the first and second group of condenser plates, which—since two measurement results are available for the phase portion of the medium in the pipe—leads to increased measurement accuracy, if the process is carried out in sequence with interchanged roles of the groups of condenser plates. And interchanging the roles of the groups of condenser plates leads to increased measurement accuracy when the separating line between the groups of condenser plates does not point exactly to the vertical axis of the pipe.

There is one special simplification of the invention process for the interchanged roles of the groups of the condenser plates in relation to the measure described, in which the current is recorded by the control and evaluation circuit on the condenser plates in the second group of condenser plates switched to the condenser plates in the first group of condenser plates, and the device for carrying out the process of the invention is characterized by the fact that the first and second groups of condenser plates are designed symmetrically relative to the vertical axis of the pipe.

The process of the invention for determining the phase portion of a flowing medium in open and closed pipes and the device for carrying out the invention process are especially suitable for use in connection with a process or a device for measuring volume flow. Since known volume flow meters, somewhat like magnetically inductive volume flow meters or ultrasound volume flow meters, only measure the speed of the flowing medium, in this process for determining the volume flow in pipes only partially filled with the liquid phase of the flowing medium, the phase portion of the liquid phase must be determined. The determination of the phase portion is, as described, guaranteed in an especially advantageous way by the process of the invention and the device for carrying out the process of the invention.

BRIEF DESCRIPTION OF THE DRAWINGS

Now there are many ways of designing and developing the invention process for determining the phase portion of a medium in open and closed pipes and the device for carrying out the process of the invention. For this, please refer to the patent claims previously explained, on one hand, and to the description of preferred invention embodiments in connection with the drawings, in which:

DESCRIPTION OF THE PREFERRED EMBODIMENTS

Figure 1:
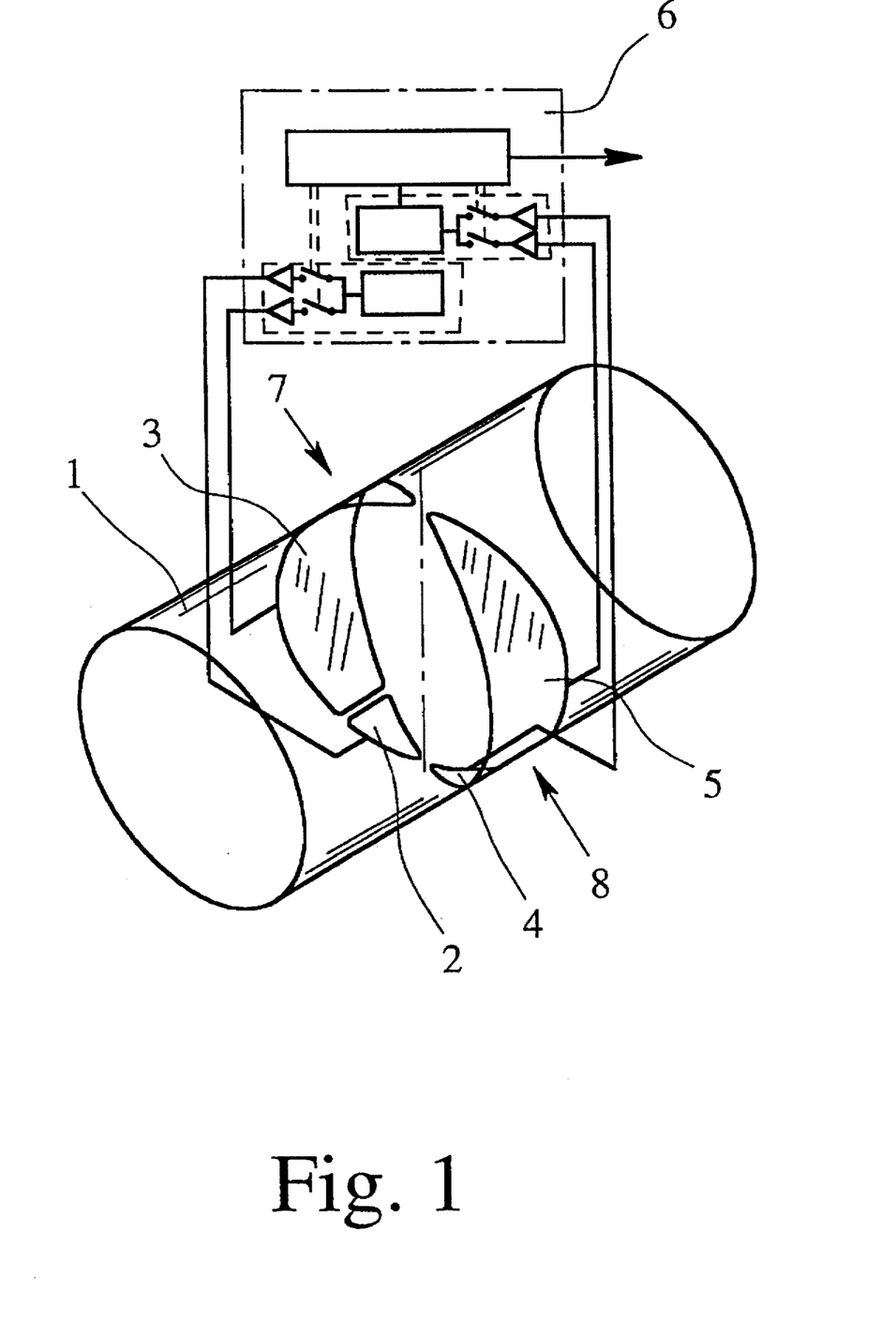
FIG. 1 is a perspective view of a first embodiment of a device for carrying out the process according to the invention.

FIG. 1 shows the first device embodiment for carrying out the invention process to determine the phase portion of a flowing medium in a closed pipe. This first embodiment has four condenser plates 2, 3, 4, 5, extending in toto basically over the entire height of a pipe 1. FIG. 1 also shows a control and evaluation circuit 6, which controls the routine for the invention process.

The condenser plates 2, 3 shown in FIG. 1 form a first group 7 of condenser plates, while the condenser plates 4, 5 form a second group 8 of condenser plates. FIG. 1 also shows clearly that the first group of condenser plates 7 and the second group of condenser plates 8 are separated from one another by the vertical line or axis of the pipe 1 shown in dashes and dots in FIG. 1.

The lowest condenser plates 2, 4 cover less height than the second condenser plates 3, 5 in the corresponding group of condenser plates 7, 8. Since the pipe 1 shown in FIG. 1 has a circular cross section, the width of the condenser plates 2, 3, 4, 5 decreases from the horizontal line H of the pipe 1 both in the direction of the base of the pipe 1 and also in the direction of the ceiling of the pipe 1, so that the width of the condenser plates 2, 3, 4, 5, is always proportional to the width of the pipe at the respective height, depending on the height of the pipe 1.

Since the device for carrying out the process in the invention shown in FIG. 1 is not combined with a device for determining volume flow, in this case it makes sense, although not shown, that the condenser plates 2, 3, 4, 5 are embedded in an insulating lining of the pipe 1.

In the first embodiment of a device for carrying out the invention process, the first group of condenser plates 7 and the second group of condenser plates 8 are designed symmetrically relative to the vertical line V of the pipe 1 (FIG. 1).

In the description of the embodiments of a device for carrying out the process according to the invention shown in the other drawing figures, the same reference numbers are used as in FIG. 1 for components in the other embodiments that are functionally identical to the first embodiment.

Figure 2:
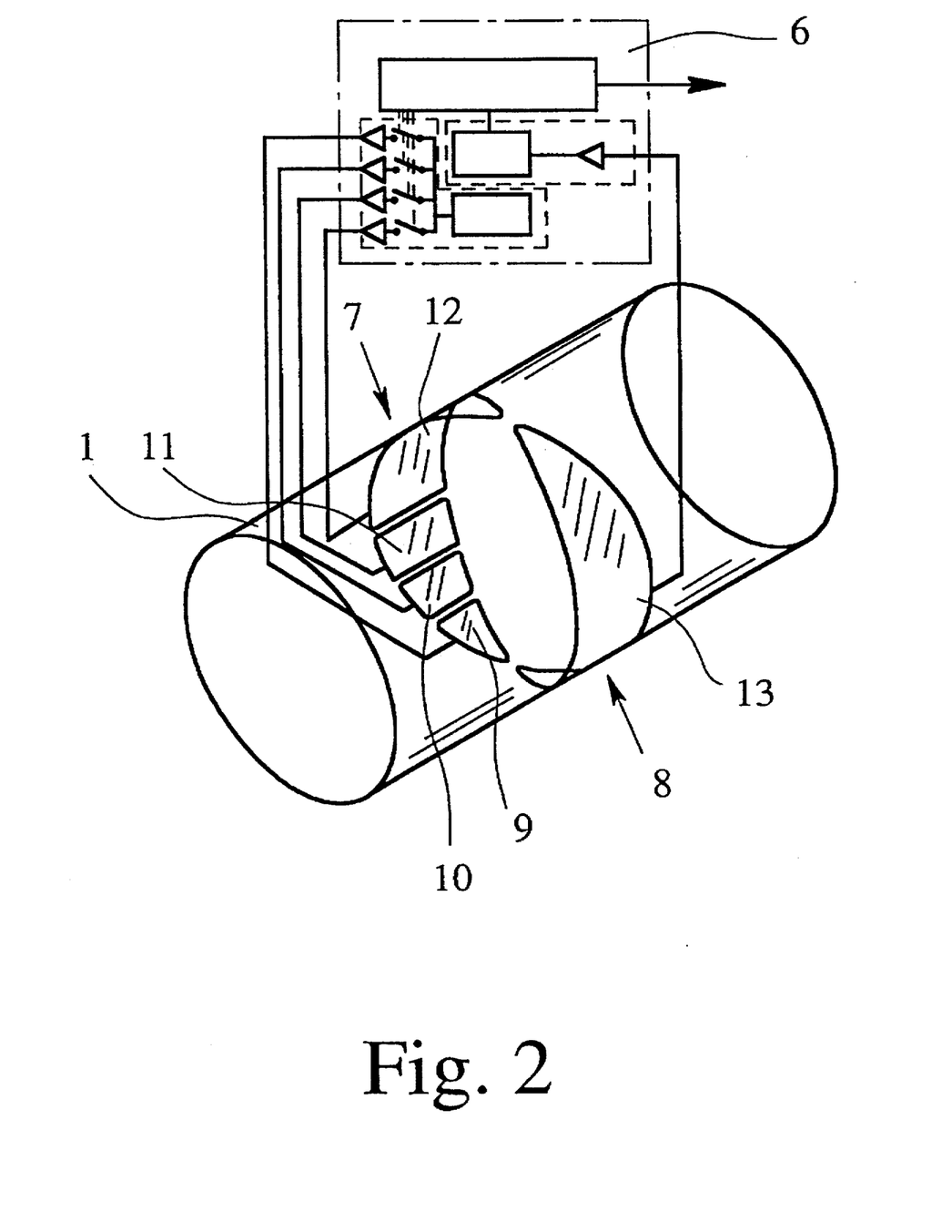
FIG. 2 is a perspective view of a second embodiment of a device for carrying out the process according to the invention.

The second embodiment of a device for carrying out the invention process shown in FIG. 2 is different from the first embodiment shown in FIG. 1 in that here four condenser plates 9, 10, 11, 12 form the first group of condenser plates 7, while the second group of condenser plates 8 consists of only one condenser plate 13.

Figure 3:
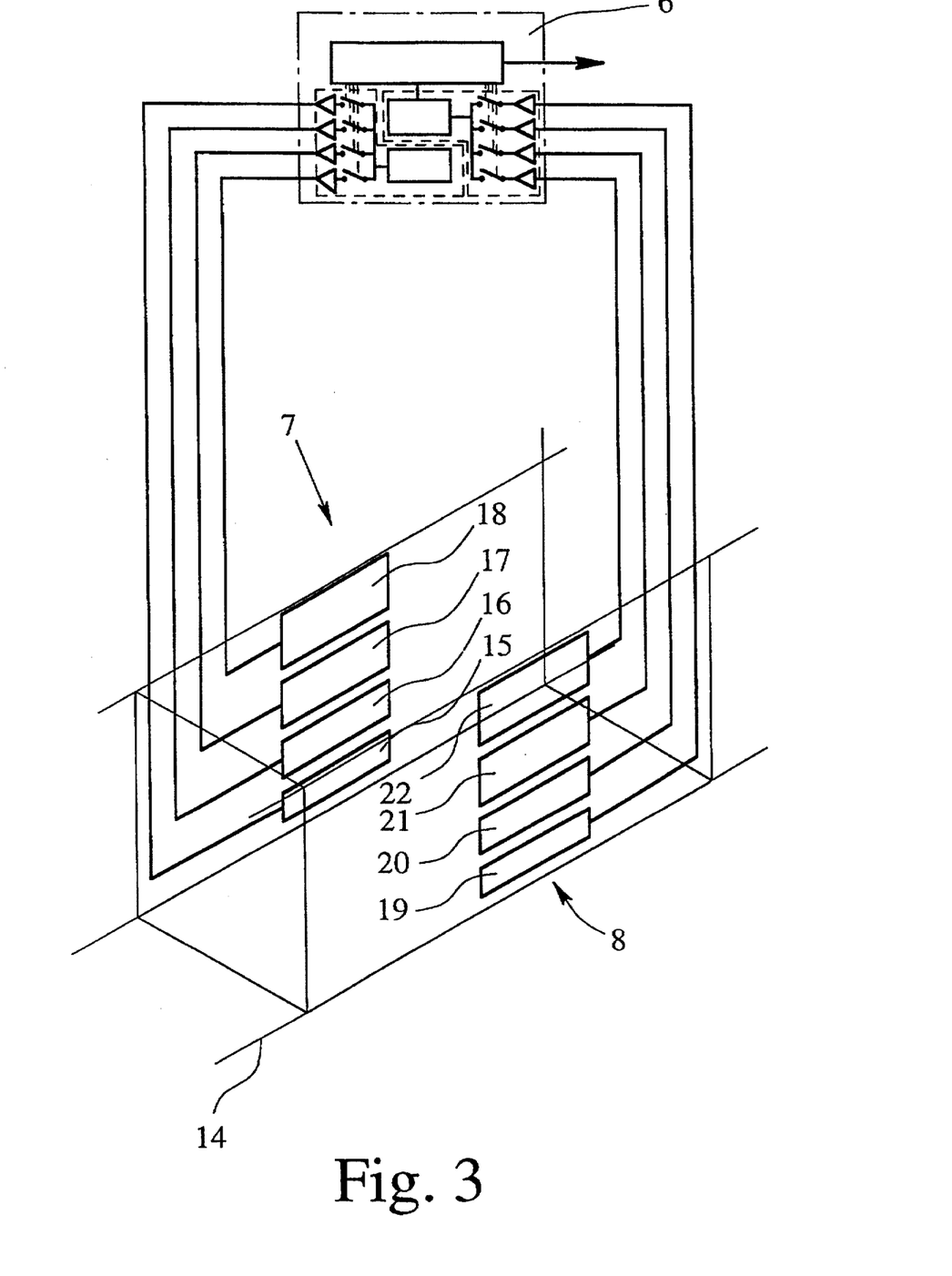
FIG. 3 is a perspective view of a third embodiment of a device for carrying out the process according to the invention.

The third embodiment of a device for carrying out the invention process shown in FIG. 3 is different from the embodiments described above, on one hand, because the pipe 14 is an open pipe, and, on the other hand, because four condenser plates 15, 16, 17, 18 form the first group of condenser plates 7 and four other condenser plates 19, 20, 21, 22 form the second group of condenser plates 8. Since in the third embodiment shown in FIG. 3, the width of the pipe 14 is independent of the height of the pipe 14, the width of the condenser plates 15, 16, 17, 18, 19, 20, 21, 22 does not change, either, depending on that height.

Figure 4:
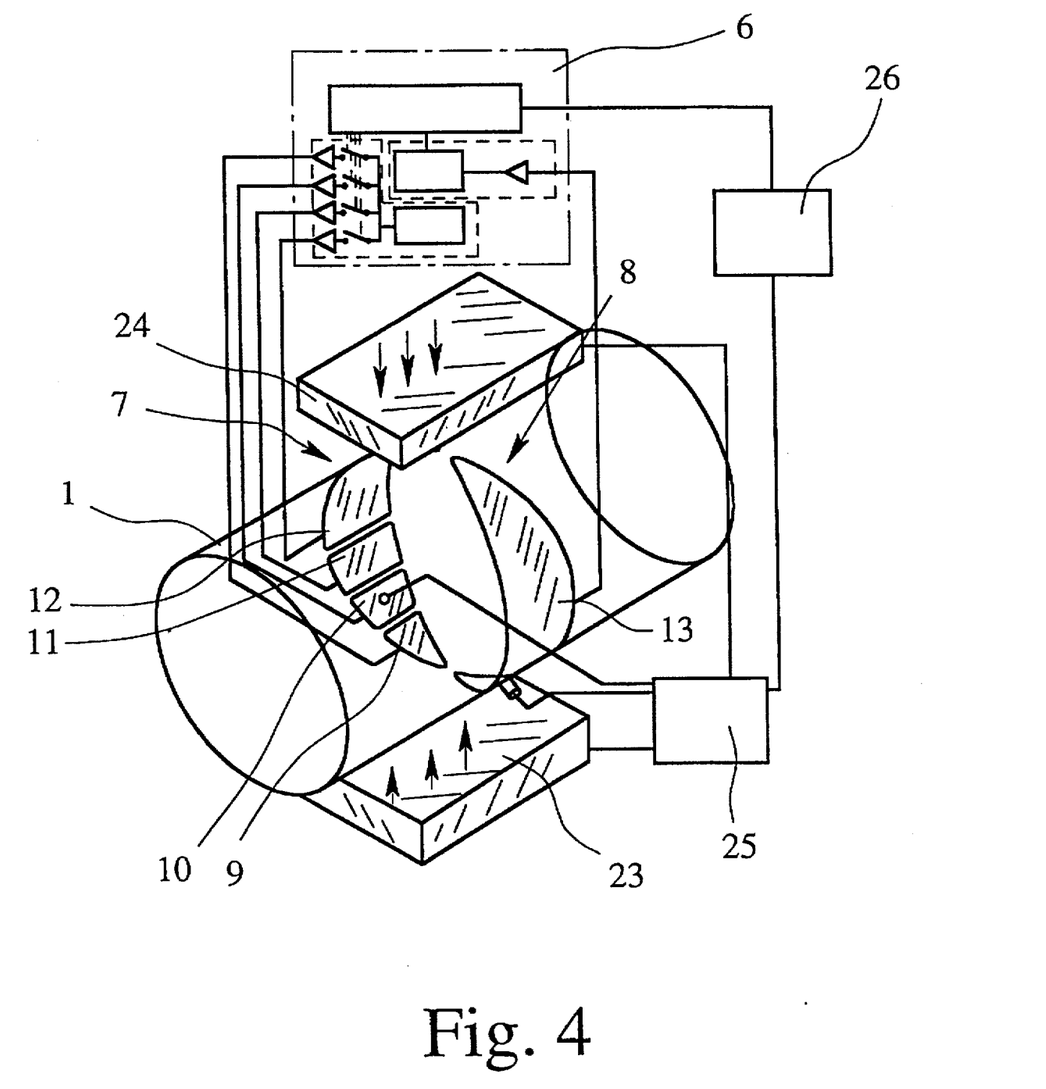
FIG. 4 is a perspective view of the second embodiment of a device for carrying out the process according to the invention in connection with a magnetically inductive volume flow meter.

In FIG. 4, the second device embodiment for carrying out the invention process is shown in connection with magnetically inductive volume flow meter. The magnetically inductive volume flow meter has two field coils 23, 24 only shown schematically, forming a vertical magnetic field perpendicular to the longitudinal axis of the pipe 1, and one processing circuit 25. The condenser plates 10, 13 of the device for carrying out the process in the invention are used as electrodes of this magnetically inductive volume flow meter. To be able to perform this function, in this second device embodiment in connection with a magnetically inductive volume flow meter, the condenser plates 10, 13 are at least partially not embedded in an insulating lining of the pipe 1 and are in immediate contact with the flowing medium in the pipe. In the magnetically inductive volume flow meter shown in FIG. 4, the processing circuit 25 controls the field coils 23, 24 in a known way and also evaluates in a known way the signals from the condenser plates 10, 13 serving as electrodes, in order to supply a measurement result for the flow speed of the flowing medium. FIG. 4 also shows a central processing circuit 26, which calculates the volume flow of the flowing medium through the pipe 1 using the measured value supplied by the control and evaluation circuit 6 for the phase portion and the measured value supplied by the processing circuit 25 for the flow speed.

Figure 5:
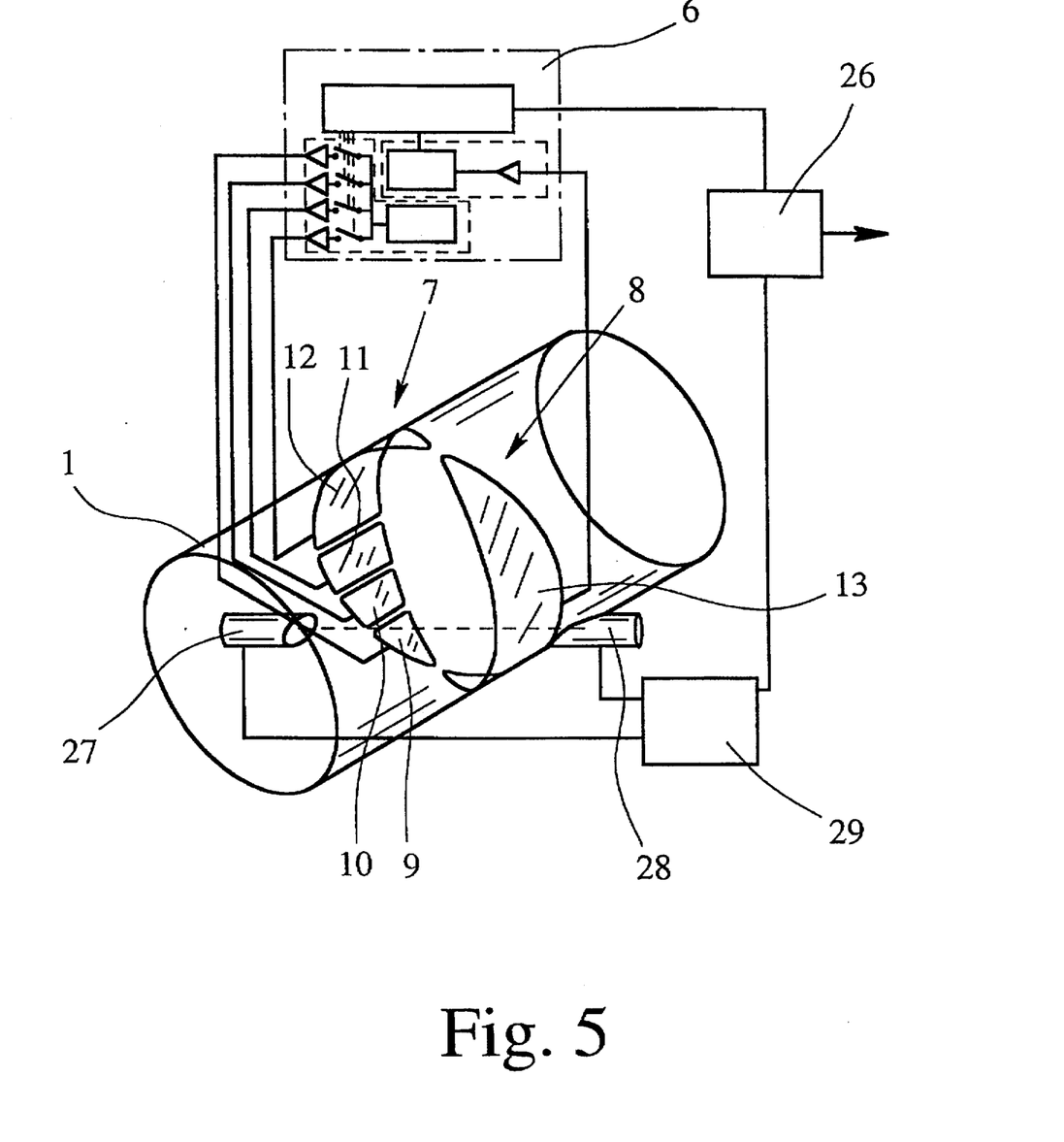
FIG. 5 is a perspective view of the second embodiment of a device for carrying out the process according to the invention in connection with an ultrasound flow meter.

Finally, FIG. 5 shows the second device embodiment for carrying out the invention process in connection with an ultrasound flow meter. This ultrasound flow meter is designed, in a known way, to be fully independent of the device for carrying out the process of the invention. On two opposite sides of the pipe 1, there are two aligned ultrasound transducers 27, 28 staggered relative to the direction of flow of the medium. The sending and receiving signals from this ultrasound transducer 27, 28 are triggered or evaluated by a processing circuit 29. As in a magnetically inductive volume flow meter, this evaluation yields a value for the speed of the flowing medium in a known way. Like the connection of a device for carrying out the process according to the invention shown in FIG. 4 with a device for measuring volume flow, in the overall device shown in FIG. 5, a central processing circuit 26 calculates the volume flow of the medium flowing through the pipe 1 from the measurement signals supplied by the control and evaluation circuit 6 and the processing circuit 29.

In conclusion, the invention process for determining the phase portion of a medium in open and closed pipes will be explained below using a mathematical representation of the physical processes on which the process of the invention is based.

The process of the invention is essentially based on evaluating the capacity between one condenser plate of the first group of condenser plates and the second group of condenser plates consisting, for example, of a single condenser plate. The capacity between these two condenser plates now basically depends on the dielectric constant $\epsilon$ of the medium found between the two condenser plates. The dielectric constant of the liquid phase is always much larger than the dielectric constant $\epsilon$ of the gaseous phase of the medium. In the invention process, the capacity between the condenser plates is determined by letting an alternating voltage run through one of the condenser plates and by measuring the current influenced by the electrical field coming out of that condenser plate at the second condenser plate. The frequency of the alternating voltage is chosen in such a way that good measurement accuracy is guaranteed for measuring the capacity and is thus more in the high-frequency range. With conductive media, besides the dielectric constant $\epsilon$, the conductivity $\sigma$ of the medium for the current flow between the condenser plats also plays a role. Like the dielectric constant $\epsilon$, the conductivity $\sigma$ is also highly dependent on the medium. The conductivity $\sigma$ can vary between 10 and 5,000 µS/cm, for example. Thus, the measurement of the capacity of the condenser plate arrangement is very strongly dependent on the electrically properties of the medium.

The current actually flowing between the condenser plates when an alternating voltage is applied is generally dependent on the impedance of the layout. The capacitive portion of the impedance is determined by the capacity of the condenser plate layout. The capacity C of two plates with a surface S and a mutual distance from D is $$C = \epsilon \cdot S/D \qquad \text{Equation 1}$$

In this case, the second portion of the impedance is determined by the resistance between the two condenser plates, which has the following value for the arrangement on which the calculation of the capacity is based:

$$R = 1/\sigma \cdot D/S \qquad \text{Equation 2}$$

The impedance Z for the layout described is found as follows:

$$z = 1/R + j\omega C, \qquad \text{Equation 3}$$

when j=imaginary unit, and
$\omega$=frequency of alternating voltage.

Thus, the following equation is for the relation of the current between the condenser plates to the voltage applied:

$$I = (\sigma + j\epsilon\omega) S/D \cdot U \qquad \text{Equation 4}$$

According to the invention, the current between the individual condenser plates in the first group of condenser plates and at least one condenser plate in the second group of condenser plates is recorded in sequence by the control and evaluation circuit. The following relations therefore apply to the individual currents measured:

$$I_1 = K_1(\sigma + j\epsilon\omega) \cdot f \cdot U. \qquad \text{Equation 5}$$

$$I_2 = K_2(\sigma + j\epsilon\omega) \cdot f \cdot U.$$

$$\vdots$$

$$I_r = K_r(\sigma + j\epsilon\omega) \cdot f \cdot U.$$

The constants $K_1, K_2, \ldots, K_r$ in Equation 5 contain the constant properties of the pair of condenser plates being controlled, like for example the geometric arrangement, the surrounding materials in the lining of the pipe, etc. Furthermore, the f in Equation 5 gives a measurement for the height to which the surface levels of the medium reaches in the condenser plate in the first group of condenser plates. If the surface level of the medium touches the lower edge of the respective condenser plate in the first group of condenser plates directly, then f is almost zero. But if the surface level of the medium reaches the upper edge of the respective condenser plate in the first group of condenser plates, f assumes the value 1.

Now, it is essential to the invention that the current in the highest condenser plate reached by the surface level of the medium be standardized using the current of the lower-lying condenser plates in the first group of condenser plates. If the current of the highest condenser plate reached by the surface level of the medium in the first group of condenser plates is standardized using the sums of the currents of the lower-lying condenser plates in the first group of condenser plates, then for the standardized current $\alpha_i$ of the highest, hence the i-est, for example, is found as follows:

$$\alpha_i = \frac{K_i(\sigma + j\epsilon\omega) \cdot f \cdot U}{\sum_{l=1}^{i-1} K_l(\sigma + j\epsilon\omega) \cdot U} = f \frac{K_i}{\sum_{l=1}^{i-1} K_l} \qquad \text{Equation 6}$$

Equation 6 now shows the special advantage of the process according to the invention that the electrical properties of the medium are mutually eliminated in the standardization of the current.

According to the process of the invention, the standardized current of the highest condenser plate reached by the surface level of the medium in the first group of condenser plates is available as a measurement for the position of the surface level of the medium relative to this highest condenser plate. Now, if the standardized current is recorded according to one embodiment of the process of the invention in a process for each condenser plate in the first group of condenser plates for a surface level of the medium on the upper and lower edge of the condenser plate, then the height of the surface level of the medium can be calculated relative to that condenser plate with a simple rule of three in a suitable embodiment of the width of the condenser plates depending on the respective height of the pipe. The height of the surface level in the pipe can obviously be determined from this height, since the positions of the condenser plates are known.

It will thus be seen that the objects set forth above, among those made apparent from the preceding description, are efficiently attained and, since certain changes may be made in carrying out the above method and in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A process for determining the phase portion of a medium having a liquid phase portion, a gaseous phase portion and a surface level seperating said phase portions in an open or closed pipe, especially for use in connection with a process for determining the volume flow, with the help of at least three condenser plates that extend basically over the entire height of the pipe and with the help of a control and evaluation circuit connected to the condenser plates, in which at least one of the condenser plates has an alternating voltage applied to it by the control and evaluation circuit and the current flowing between the condenser plate with the voltage applied to it and at least one other condenser plate is recorded by the control and evaluation circuit characterized by the fact that: the current between at least two condenser plates is recorded by the control and evaluation circuit from two different groups of condenser plates separated by the vertical the current between individual condenser plates in the first group of condenser plates and at least one condenser plate in the second group of condenser plates is recorded by the control and evaluation circuit in sequence; the current of the highest condenser plate reached by the surface level of the medium in the first group of condenser plates is standardized by the control and evaluation circuit using the currents of the lower-lying condenser plate in the first group of condenser plates; and the standardized current of the highest condenser plate reached by the surface level of the medium in the first group of condenser plates is evaluated as a measurement for the position of the surface level of the medium relative to the highest condenser plate reached by the surface level of the medium in the first group of condenser plates.

2. The process according to claim 1, characterized by the fact that the current of the highest condenser plate reached by the surface level of the medium in the first group of condenser plates is standardized using the sum of the currents of the lower-lying condenser plates in the first group of condenser plates.

3. The process according to claim 2, characterized by the fact that the currents of all sequences of condenser plates in the first group of condenser plates beginning with the lowest condenser plate in the first group of condenser plates are recorded in sequence by the control and evaluation circuit.

4. The process according to one of claims 1 to 3, characterized by the fact that in a calibration process for each condenser plate in the first group of condenser plates, the standardized current is recorded at a surface level of the medium on the upper edge of the condenser plate.

5. The process according to claim 4, characterized by the fact that in the calibration process for each condenser plate in the first group of condenser plates, the standardized current is recorded at a surface level of the medium on the lower edge of the condenser plate.

6. The process according to claim 4, characterized by the fact that the standardized current for each condenser plate in the first group of condenser plates between a surface level of the medium on the lower edge and a surface level of the medium on the upper edge of the respective condenser plate is assigned linearly to the height of the medium relative to the respective condenser plate by the control and evaluation circuit.

7. The process according to one of claim 1 to 3, characterized by the fact that the current is recorded by the control and evaluation circuit with the condenser plates in the second group of condenser plates switched together.

8. The process according to one of claims 1 to 3, characterized by the fact that the current is recorded by the control and evaluation circuit with the condenser plates in the second group of condenser plates switched corresponding to the condenser plates in the first group of condenser plates.

9. The process according to one of claims 1 to 3, characterized by the fact that the volume flow is determined directly from the height of the surface level of the medium when the surface level of the medium is low.

10. The process according to one of claims 1 to 3, characterized by the fact that the conductivity and/or the dielectric constant of the medium is determined by the control and evaluation circuit.

11. A device for carrying out the process defined in claim 1 comprising at least three condenser plates (2–5; 9–13; 15–22) extending in toro basically over the entire height of the pipe (1) and with a control and evaluation circuit connected to the condenser plates, characterized by the fact that at least two and preferably four condenser plates (2; 3; 9–12; 15–18) form a first group (7) of condenser plates, at least one condenser plate (4; 5; 13; 19–22) forms a second group (8) of condenser plates, all said condenser plates (2–5; 9–13; 15–22) are assigned to one or the other of said two groups (7; 8) of condenser plates, and the first group (7) of condenser plates and the second group (8) of condenser plates are separated from one another by the vertical line of the pipe (1).

12. The device according to claim 11, characterized by the fact that the lowest condenser plate (2; 9; 15) in the first group of condenser plates (7) covers a lower height than the other condenser plates (3; 10–12; 16–18) in the first group of condenser plates (7).

13. The device according to claim 11 or 12, characterized by the fact that the width of the condenser plates (2–5; 9–13; 15–22) is always proportional to the width of the pipe (1) at the respective height, depending on the height of the pipe (1).

14. The device according to one of claims 11 or 12, characterized by the fact that the condenser plates (2–5; 9–13; 15–22) are embedded at least basically in an insulating lining of the pipe (1).

15. The device according to claim 14, characterized by the fact that one condenser plate (10) that is in contact with the medium in the first group of condenser plates (7) and one condenser plate (13) in the second group of condenser plates (8) serve as electrodes for a magnetically inductive volume flow meter.

16. The device according to one of claims 11 or 15, characterized by the fact that two and preferably four condenser plates (4, 5; 19–22) form the second group of condenser plates (8).

17. The device according to claim 16, characterized by the fact that the first group of condenser plates (7) and the second group of condenser plates (8) are designed symmetrically relative to the vertical axis of the pipe (1).

* * * * *